United States Patent [19]

Frank et al.

[11] 4,303,419

[45] Dec. 1, 1981

[54] METHOD AND COMPOSITION FOR DETERMINATION OF N-NITROSAMINES

[75] Inventors: Clyde W. Frank; Paul J. Nord; Robert D. Cox, all of Iowa City, Iowa

[73] Assignee: University of Iowa Research Foundation, Iowa City, Iowa

[21] Appl. No.: 166,382

[22] Filed: Jul. 7, 1980

Related U.S. Application Data

[62] Division of Ser. No. 108,236, Dec. 28, 1979, Pat. No. 4,256,462.

[51] Int. Cl.$^3$ .................... B01D 19/00; G01N 21/76; G01N 35/08; G01N 37/00
[52] U.S. Cl. ........................................ 55/185; 55/518; 261/DIG. 19; 422/52; 422/81; 422/82
[58] Field of Search ................ 55/159, 178, 185, 519, 55/527; 261/DIG. 19; 252/361; 422/68, 81, 82, 52, 171, 172

[56] References Cited

U.S. PATENT DOCUMENTS

| | | | |
|---|---|---|---|
| 2,967,764 | 1/1961 | Skeggs | 422/82 |
| 3,335,549 | 8/1967 | Hendrix | 55/178 |
| 3,631,654 | 1/1972 | Riely et al. | 55/159 |
| 3,650,093 | 3/1972 | Rosenberg | 55/159 |
| 3,754,870 | 8/1973 | Carnahan et al. | 422/171 |
| 3,930,805 | 1/1976 | Vogt et al. | 422/172 |
| 4,149,860 | 4/1979 | Kulik | 55/159 |

Primary Examiner—Michael S. Marcus
Attorney, Agent, or Firm—Zarley, McKee, Thomte, Voorhees & Sease

[57] ABSTRACT

N-nitrosamines are reacted with a denitrosating agent to cleave the N-NO bond and yield nitric oxide which may be analyzed to determine both qualitatively and quantitatively, the N-nitrosamine content of a test sample. The denitrosating reagent has the advantage of being useful, even in the presence of substantial amounts of water, and comprises a mixture of glacial acetic acid and a concentrated inorganic acid which is either phosphoric acid or sulfuric acid. The volume ratio of glacial acetic to concentrated acid is within the ratio of from 1:2 to 5:1. This acid component mixture is combined with from about 0.1% to about 5% by weight of soluble inorganic bromide or iodide salt.

5 Claims, 3 Drawing Figures

METHOD AND COMPOSITION FOR DETERMINATION OF N-NITROSAMINES

This is a division of application Ser. No. 108,236, filed Dec. 28, 1979, now U.S. Pat. No. 4,256,462.

BACKGROUND OF THE INVENTION

N-nitrosamines have become of more active concern in recent times due to the recent technology revealing that some of these compounds are active carcinogens. These compounds have been found in many common foods. For example, N-nitrosamines have been found in nitrite treated meats such as bacon, and recent reports have discovered their presence in beverages such as scotch and beer. There is, therefore, a continuing need for techniques to determine, both quantitatively and qualitatively, the N-nitrosamine levels in a variety of compositions to which man is continually exposed.

N-nitrosamines have the following basic structure:

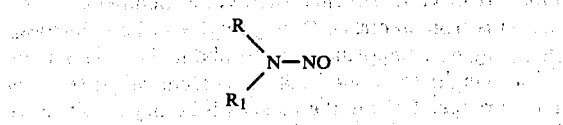

wherein both R and $R_1$ may represent a variety of organic or substituted organic moieties. In analyzing such compounds to determine not only their presence but also the level of concentration of the compounds present in any test sample, the bond between the nitrogen and the NO moiety is cleaved to produce nitric oxide gas which is removed from the reaction solution.

This bond is cleaved in an acid catalyzed reaction. Commonly in the past, this denitrosation reaction has employed as the reagents, glacial acetic acid with HBR; see, for example, Eisenbrand, G., et al., *Arzneim-Forsch*, 20, 1513 (1970). This is, however, a slow reaction and the presence of water in the test sample interferes with the reaction to substantially prevent liberation of nitric oxide gas. Other reported methods include those of Drescher, S., and Frank, C. W., *Anal. Chem.*, 50, 2118–2121 (1978) and Downes, M. J., Edwards, M. W., Elseg, T. S., and Walters, C. L., *Analyst* 101 742 (1976). The Drescher et al. method employs methylene chloride solvent, glacial acetic acid and HBR. The Downes, et al. method employs 1,2 dichloroethane solvent.

In these methods, as well as other methods of denitrosation apparently being used, a significant problem is that the reactions employed are intolerant to even small amounts of water present in the reaction system or the test samples. That is to say, the presence of water inhibits the cleavage reaction from occurring and accordingly, insufficient amounts of nitric oxide are released within a reasonable period of time to conduct the analysis.

Accordingly, a primary object of this invention is to develop a denitrosating reagent composition which is usable even in the presence of water to effectively cleave the N—NO bond of an N-nitrosamine.

Another object of this invention is to provide an improved denitrosating reagent which not only is usable in the presence of water, but also reacts quickly to provide NO gas for further use in the analysis being conducted.

An even further object of this invention is to provide a method of denitrosating N-nitrosamines which employs the improved denitrosating reagent compositions of the invention.

Another object of this invention is to provide an improved method of determination of N-nitrosamines in a test sample, which method is usable even in the presence of large amounts of water in the test sample.

A still further object of this invention is to provide an improved degassing cell which is specifically designed for use with small, microliter amounts of liquid, to efficiently and effectively strip gaseous components dissolved in the small amount of liquid.

An even further object of the invention is to provide a detection method, means, and apparatus for specific use with N-nitrosamine analysis which is quick to operate, efficient to operate, tolerant to water in the test samples, and which accurately allows qualitative and quantitative detection of N-nitrosamines.

The method composition means and device for accomplishing the stated objectives of this invention, as well as others, will become apparent from the detailed description of the invention which follows.

SUMMARY OF THE INVENTION

Figure 1:
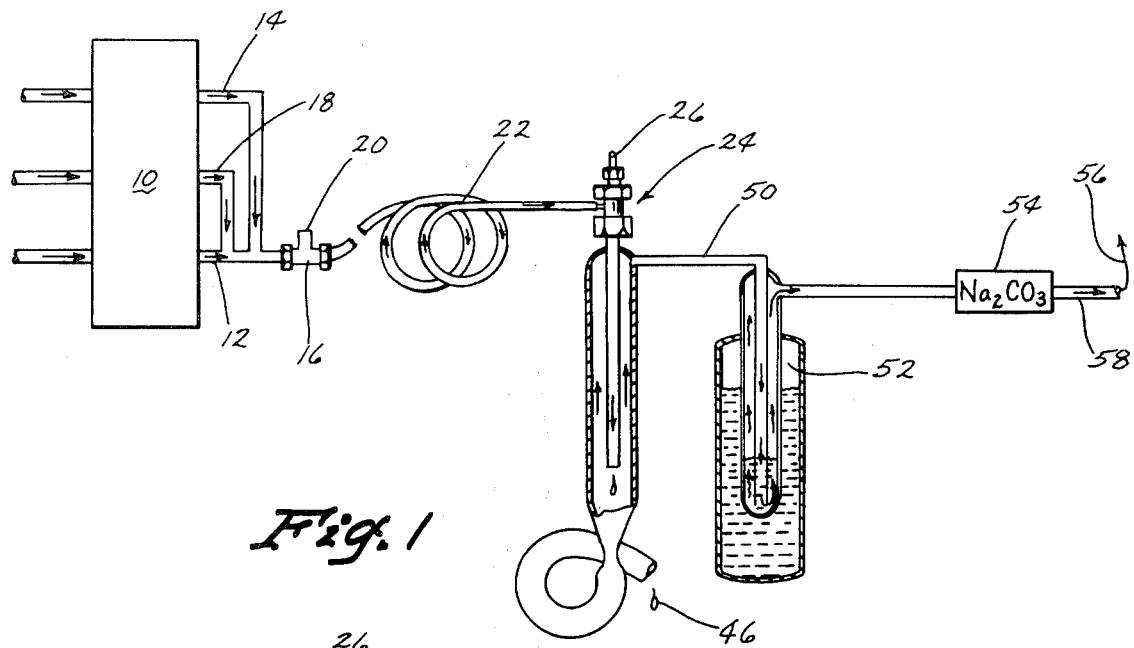
FIG. 1 is a flow chart schematically illustrating, for illustrative purposes, an overall analysis, as practiced in accordance with the method of this invention.

An improved method, device and composition for use in determination of N-nitrosamines. The denitrosating composition chemically cleaves the N—NO bond at a rapid rate, and is usable in systems which have water present. The composition comprises a mixture of glacial acetic acid and concentrated inorganic acid which is either phosphoric or sulfuric, the ratio of the glacial acetic acid to the other acid being within the range of from 1:2 to 5:1, with this acid mixture being combined with from about 0.1% to about 5% by weight of an inorganic water soluble bromide or iodide salt. The device is an improved degassing cell specifically designed for use with small liquid volumes in order to strip, for example, NO gas dissolved in the reacting reagents.

DETAILED DESCRIPTION OF THE INVENTION

The determination of N-nitrosamines by high performance liquid chromatography can be divided into four basic steps. In the first step, there is separation of the various N-nitrosamines with a suitable column and solvent. In this step, the test sample is pumped through the liquid chromatography column; the amount of time that it takes for the separation, and for the material to come out of the column along with the column solvent system, can be compared with known standards to determine, qualitatively, which N-nitrosamines are present. The compounds which are now dissolved in the column effluent are then treated in the second step which involves chemically cleaving the N—NO bond in the N-nitrosamine to give nitric oxide (NO) gas.

In the third step, the solution containing the nitric oxide gas is degassed, commonly with helium, to remove the nitric oxide.

Finally, in a fourth step, quantitative determination of the NO is conducted via instruments such as Bendix Nitrogen Analyzers which determine NO via its chemiluminescent reaction with ozone. For the specific means and mode of operation of an NO analyzer, see for example, the Operation Service Manual for Bendix Model 8101-B Oxides of Nitrogen Analyzer, Code No. B1357 TM473 which is incorporated herein by reference. It is, of course, to be understood that this NO Analyzer is merely mentioned for illustrative purposes and other NO analyzers such as those made by Waters, Hewlett-Packard, and Columbia Instruments, could also conveniently be used.

The inventions disclosed herein basically involve the second step, namely, chemically cleaving the N—NO bond and the third step, degassing of the solution.

Any useful method for chemically cleaving the N—NO bond of N-nitrosamines, should have a rapid rate of reaction and be adaptable to specific solvent systems used in the liquid chromatographic separation step. Further, the amount of NO liberated should be directly proportional to the initial amount of N-nitrosamines present. Additionally, this system must have tolerance to water since many test samples contain water.

Prior methods for cleaving the N—NO bond of N-nitrosamines have been examined and found not satisfactory. Such methods in most instances are not usable in water systems because the denitrosation reaction fails to occur in the presence of water; or the method is extremely slow taking hours which makes it uneconomical; or the method has both deficiencies.

The denitrosating reagent composition of this invention is not only tolerant of water in the system, but also compatible with the common solvent systems used in liquid chromatographic separation, such as ethyl alcohol, methyl alcohol, methylene chloride, ethyl acetate, hexane, chloroform, and even in some cases, water; and, the reaction is kinetically rapid.

The reaction to cleave the N—NO bond is an acid catalyzed reaction which occurs in the presence of either the bromo- or iodo- ion (X⁻) in accordance with the following equation:

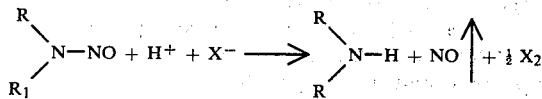

The composition to accomplish this comprises a mixture of an acid component which is in part glacial acetic acid and in part a concentrated inorganic acid which may be either phosphoric acid or sulfuric acid, in combination with from about 0.1% to about 5% by weight of the entire composition being an inorganic water soluble bromide or iodide salt.

The volume ratio of the glacial acetic acid to the other acid can be within the range of from about 1:2 to about 5:1, but is preferably within the range of from about 1:1 to about 3:1 with the best results to date being when the volume ratio of glacial acetic acid to the other acid is about 2:1.

The concentration of the concentrated inorganic acid which is either phosphoric acid or sulfuric acid, should be at least 12 molar, and as a general guideline, may be within the range of from 12 molar to 18 molar. Commercially available phosphoric and sulfuric acids sold as "concentrated" are very satisfactory, as purchased.

It has been found that in the event the acid concentrations are lower than those specified herein, the reaction is simply too slow to be commercially practicable. On the other hand, if they are greater than those specified herein, no additional advantage is seen. Thus, the upper limit is a practical one based on economics more than anything else.

In the reaction shown in the equation above, "X" represents either a bromide ion or an iodide ion. It cannot be chloride ion since the reaction will not cleave the N—NO bond in the presence of chloride ion. Bromide ion works but is somewhat slow. Most preferred is the iodide ion.

The cation of the bromide or iodide salt is not critical, except that the salt must be an inorganic water soluble salt. Suitable salts are alkali metal salts or alkaline earth metal salts. The most satisfactory is sodium iodide.

The concentration of the salt which has been found most effective to enhance the overall denitrosating reaction is from about 0.1% by weight of the denitrosating reagent composition up to about 5%, with from 0.2% weight to about 3.0% by weight being the preferred range. To date the most satisfactory results have been at about 0.5% by weight.

Either phosphoric acid or sulfuric acid meeting the criteria previously specified herein may be employed as the second acid component. Of course, mixtures of the two could also be employed, although no particular advantage is seen in doing so. It has, however, been found essential that the second acid component be either phosphoric or sulfuric. In experimentation to date, these are the only acids when combined with glacial acetic, which provide a denitrosating reagent which is tolerant to water in the system.

As heretofore mentioned, typically N-nitrosamine analysis involves four basic steps. For convenience and clarity of description, those basic steps will be described briefly herein, with reference to FIG. 1.

As shown in FIG. 1, a pump 10, pumps concentrated acids for example, acetic acid via line 12 and phosphoric acid via line 14, to a common T-union or junction 16. The iodide solution is pumped via line 18 to the same T union 16. Column effluent from the separation of N-nitrosamines in a test sample, which contains the N-nitrosamines, is injected into the T union 16 at line 20. If the column effluent contains water, and concentrated sulfuric acid is employed, it may be used in concentrated form. However, if the column effluent injected at line 20 contains no water it is preferred that some water be added to the concentrated sulfuric, for example (50:50 H₂O to Con. H₂SO₄) to prevent reduction of the iodide ion to iodine. The denitrosating reagent composition and the solvent, for example ethyl acetate, are then simultaneously pumped through mixing and reacting coil 22, wherein the reagents are intimately admixed.

In actual use, the lines leading into and out of pump 10 may be viton tubing and the pump may be a technicon auto-analyzer pump which rolls over the tubing to create the pumping pressure. The reagents are pumped through the mixing and reacting coil 22 which may, for example, be about three feet long. This provides sufficient time for the reaction to go sufficiently to completeness to allow liberation of sufficient quantities of nitric oxide.

The nitric oxide is by and large dissolved in the denitrosating reagent composition and the solvent effluent which are together emitted from the mixing and reaction coil 22. Next, the material passes into the degassing cell, generally depicted in FIG. 1 at 24. In the degassing cell, helium as a stripping gas is introduced via line 26 in order to strip the nitric oxide from the solution.

Figure 2:
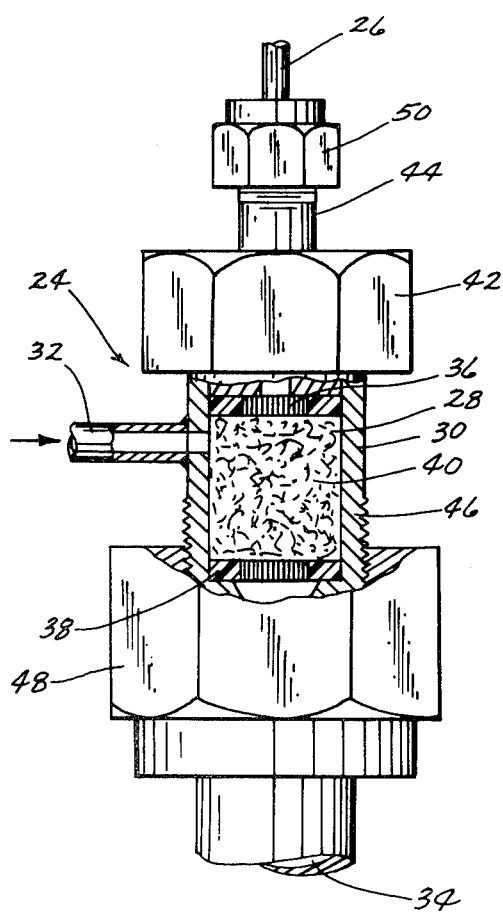
FIG. 2 is an exploded, fragmentary elevational view, with certain parts broken away, to show the degassing cell of this invention.

Reference is made to FIG. 2 for the specifics of the degassing cell. The degassing cell is specifically designed for micro-analysis techniques. It also provides a low dead volume within the degassing cell chamber, and yet provides high efficiency from the standpoint of mixing and gas stripping.

In its simplest terms, the degassing cell has positioned at its top end a gas inlet line 27 which has an inlet into an interior chamber 28 defined by exterior wall 30. Downstream from line 26 and opening into exterior wall 30 is liquid inlet opening 32; and downstream from liquid inlet opening 32 is materials exit line 34.

As can be best seen in FIG. 2, chamber 28 has adjacent the inlet opening of port 26, a first porous frit 36, and in like manner, positioned adjacent exit opening 34 is second porous frit 38. Frits 36 and 38 are porous membrane materials, in some cases metallic and in some cases glass, through which a liquid will freely flow, with the frits causing some turbulence to enhance mixing. The remaining portion of chambers 28 between frits 36 and 38 is substantially completely filled with a porous filler material such as crushed glass 40. The purpose of the filler material, such as crushed glass 40, is to decrease the dead volume within chamber 28 and to increase mixing and turbulence, thus allowing easier stripping of the nitric oxide gas.

The degassing cell as shown is comprised of just four components. The first member is an upper hexagonal nut 42 and an upper smaller stem 44 and a lower, longer stem 46. Both stems are threaded. Lower stem 46 is threadably received into a second nut member 48. A smaller locking nut 50 is attached to the upper stem 44 of first member 42 and has attached to it the helium inlet line 26. The central hollow portion of lower stem 46 and member 48 define interior chamber 28.

In practice the test sample and reagent mixture enters chamber 28 via line 32 and impinges against the crushed glass 40, which is preferably 30 to 60 mesh. Helium is introduced in a turbulent manner through line 26 which passes through top frit 36 and inter-mixes with the sample and reagent mixture in chamber 28. It too, impinges against the crushed glass 40. All of the reagents and the helium as well, pass downstream through frit 38 and into line 34. The waste reagents 46 pass out of the system via line 48 with the mixture of helium and nitric oxide escaping into line 50.

Line 50 leads to solvent trap 52 and through water trap 54 with the helium thereafter escaping upwardly and out as depicted at line 56, and the nitric oxide, as depicted at line 58, going to the nitric oxide analyzer.

Of course, as those skilled in the art readily understand, a variety of means of removal of the solvent from the system may be employed. The number of traps 52, as well as traps 54, may be varied, these not being important features of the invention.

The degassing cell has been found peculiarly advantageous in stripping nitric oxide from small liquid volumes. It can, of course, be used for stripping other gases. The frits have been found advantageous, particularly where they substantially cover the gas inlet opening and the gas exit line so that all materials entering and leaving the chamber via these lines must pass through them. This increases turbulence and stripping efficiency.

The NO analyzer and its use is conventional. Basically, such analyzers operate on the principle of photometric detection of the chemiluminescence resulting from the gas phase reaction of nitric oxide with ozone. This reaction is peculiarly unique to nitric oxide and ozone. The instrument then gives a readout number which can be compared with readouts on control charts to provide quantitatively the level of N-nitrosamine present. In the examples presented hereinafter, the readouts from a Bendix Model 8101B in nitrogen analyzer were recorded via use of a graph-like recorder. The area under the recorded peaks was integrated to provide the resulting figures. These response values are a measure of the relative amounts of nitric oxide present.

The following examples are offered to further illustrate the process of the invention, use of the denitrosating agent and, as well, use of the degassing cell.

In each of the example, a denitrosating reagent of 1% sodium iodide in a 2:1 mixture of glacial acetic acid and concentrated 18 molar phosphoric acid, unless otherwise specified, was used. The apparatus illustrated schematically in FIG. 1 was employed with the coil 22 being a five foot reaction coil of 0.50 inches inside diameter, and with the T union joint member 16 being a 1/16th inch stainless steel T union. A solvent flow ratio of approximately 3.4 milliliters per minute was used. Known N-nitrosamine samples were tested in order to determine the effect of added water in the denitrosating reagent system. The degassing cell 24 previously described herein was employed in the system. The N-nitrosamines were dissolved in methylene chloride solvent.

TABLE I (Examples 1-4)
Denitrosating with 1% sodium iodide in acetic acid and phosphoric acid (2:1)

| Example | Nitrosamine $\times 10^{-9}$ moles | N-Nitrosodiphenylamine | N-Nitrosodibutylamine | N-Nitrosopryrolidine |
|---|---|---|---|---|
| 1. | .5 | 508 | 537 | 1347 |
| 2. | 1.0 | 1337 | 1128 | 3008 |
| 3. | 1.5 | 2039 | 1982 | 4950 |
| 4. | 2.0 | 2946 | 2478 | — |

In the table the response values represent measured area of peaks which were integrated to determine the quantity of N-nitrosamine. The higher the response value, the greater the efficiency of the denitrosating reagent.

(EXAMPLES 5-11)

In order to determine the tolerance of the denitrosating reagent to water added to the system, incremental amounts of water on a weight basis of the test samples was added and the effect determined. In all instances, unless stated to the contrary, conditions for the following examples were the same as in examples 1 through 4.

TABLE II

Effect of Water added to Acetic Acid:Phosphoric Acid (2:0)
(1% NaI Reagent)

| Example | % $H_2O$ Added | $1 \times 10^{-9}$ Moles N-Nitrosodiphenylamine Integrated Peak Area |
|---|---|---|
| 5. | 0 | 980 |
| 6. | 10% | 757 |
| 7. | 15% | 819 |

TABLE II-continued

Effect of Water added to Acetic Acid:Phosphoric Acid (2:0) (1% NaI Reagent)

| Example | % H$_2$O Added | $1 \times 10^{-9}$ Moles N-Nitrosodiphenylamine Integrated Peak Area |
|---|---|---|
| 8. | 20% | 1375 |
| 9. | 30% | 1283 |
| 10. | 50% | 1852 |
| 11. | 80% | 2128 |

As can be seen from an examination of examples 5 through 11, in fact as one increased the amount of water the detection response increased showing an increase in efficiency of the denitrosating agent with water being present. It is believed that this is due to an increase in the degassing efficiency of the more aqueous systems.

(EXAMPLES 12-15)

In the following examples, conditions stated for examples 1 through 4 were used, unless specified to the contrary. A variety of samples were run using in one instance 1% sodium iodide with the acetic acid:phosphoric acid mixture, and in another instance 0.66% sodium iodide. In order to show variability of the solvent, the solvent was changed from methylene chloride to ethyl acetate when using the 0.66% sodium iodide. The results are shown in Table III below.

TABLE III

Denitrosation of N-Nitrosodiphenylamine Phosphoric Acid Solvent Systems

| Example | N-nitrosodi-phenylamine ($\times 10^{-9}$ moles) | 1% NaI Acetic Acid:Phosphoric (2:1) | .66% NaI Acetic Acid:Ethyl Acetate Phosphoric (4.3:2) |
|---|---|---|---|
| 12. | .5 | 508 | 589 |
| 13. | 1.0 | 1337 | 1380 |
| 14. | 1.5 | 2039 | 2150 |
| 15. | 2.0 | 2946 | 3039 |

As can be seen in each instance, the use of ethyl acetate solvent had no significant impact or effect upon the denitrosating reaction.

When in the above examples bromo salts are substituted for the iodo salts, the reactions are found to occur but at a significantly slower rate. Particularly for the sodium iodide salt, the reaction will occur within one minute, whereas, when bromo salts are substituted, the reaction times are considerably longer, such as five minutes.

EXAMPLE 16

Figure 3:
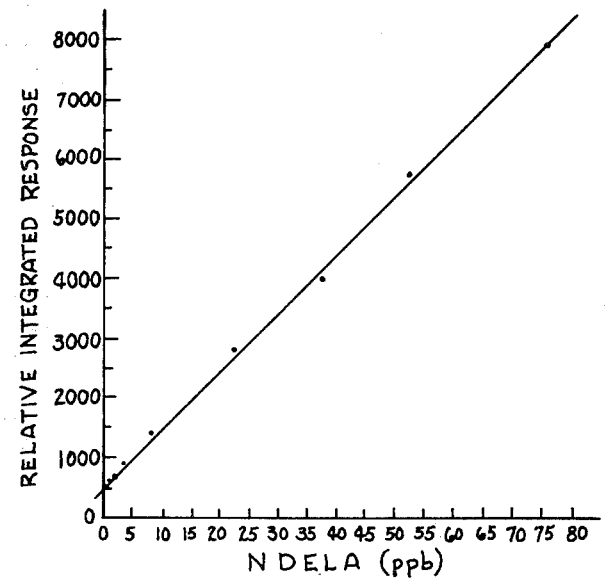
FIG. 3 is a plot of concentration of N-nitrosodiethanolamine (NDELA) versus integrated response with respect to the runs of Example 16.

The following example is presented to demonstrate the use of sulfuric acid as an inorganic acid in the reaction medium. The reaction solution consisted of Acetic acid 58% (v/v), Sulfuric acid 16% (v/v), water 22% (v/v) and sodium iodide 0.4% (w/v). Various amounts of N-nitrosodiethanolamine (NDELA) were added to this solution and the amount of NO liberated was determined by chemiluminescence. The integrated responses obtained for varying amounts of this compound are presented below. Also presented in FIG. 3 is a plot of concentration of NDELA versus integrated response. The plot proved to be quite linear with a correlation coefficient of $r = 0.9995$. The linearity of the response demonstrates high denitrosation efficiency.

| NDELA Concentration (ppb) | Integrated Response |
|---|---|
| 0.00 | 500 |
| 0.76 | 520 |
| 1.51 | 600 |
| 3.78 | 890 |
| 7.57 | 1303 |
| 22.70 | 2800 |
| 37.84 | 4000 |
| 53.00 | 5750 |
| 75.68 | 7900 |

What is claimed is:

1. A degassing cell designed specifically for handling very small liquid volumes and separation of gas from said liquid for subsequent analytical determinations, said cell being particularly adapted to use in continuous flow, small volume, analysis systems, comprising:

a small volume vessel having an exterior wall which defines an internal mixing chamber, said vessel having a gas inlet means at one end thereof adapted to connect to a gas supply source, a liquid inlet means downstream of said gas inlet means and a materials exit means at the other end thereof;

a first porous frit in said mixing chamber adjacent said gas inlet means and situated across the longitudinal axis of said vessel;

a second porous frit positioned in said chamber downstream of said liquid inlet means, adjacent said materials exit means and situated across the longitudinal axis of said vessel, said liquid inlet means being connected to said vessel wall at a point between said first and second porous frits; and;

the remaining interior space of said mixing chamber being substantially filled with filler material to decrease the chamber volume, put porosity in said chamber and facilitate mixing and gas removal.

2. The degassing cell of claim 1 wherein said porous filler material is crushed glass.

3. The degassing cell of claim 1 wherein said frits are of such dimension that they completely cover the gas inlet opening and the gas exit line so that all material entering said chamber through said gas inlet and exiting through said exit must pass through said frits.

4. The degassing cell of claim 1 wherein said porous frits are glass frits.

5. The degassing cell of claim 4 wherein said porous frits are metal frits.

* * * * *